US007005281B2

(12) United States Patent
Öhrlein et al.

(10) Patent No.: US 7,005,281 B2
(45) Date of Patent: Feb. 28, 2006

(54) ENZYMATIC PROCESS FOR PREPARING ORGANOSILICON GROUP CONTAINING PHOTOINITIATORS

(75) Inventors: Reinhold Öhrlein, Rheinfelden-Herten (DE); Kai-Uwe Schöning, Oberwil (CH); Gabriele Baisch, Binzen (DE); Jemima Schmidt, Schopfheim (DE); Gisèle Baudin, Allschwil (CH); Tunja Jung, Rheinfelden-Herten (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 10/506,698

(22) PCT Filed: Feb. 25, 2003

(86) PCT No.: PCT/EP03/01896

§ 371 (c)(1),
(2), (4) Date: Sep. 2, 2004

(87) PCT Pub. No.: WO03/074718

PCT Pub. Date: Sep. 12, 2003

(65) Prior Publication Data

US 2005/0124820 A1    Jun. 9, 2005

(30) Foreign Application Priority Data

Mar. 6, 2002    (EP) .................................. 02405171

(51) Int. Cl.
*C12P 7/62* (2006.01)
*C12P 7/26* (2006.01)
*C12P 13/02* (2006.01)

(52) U.S. Cl. ...................... 435/135; 435/128; 435/129; 435/132; 435/136; 556/430; 556/436; 556/437; 556/450

(58) Field of Classification Search ................ 435/135, 435/136, 132, 129, 128; 556/450, 430, 436, 556/437
See application file for complete search history.

(56) References Cited

U.S. PATENT DOCUMENTS 6,288,129 B1    9/2001  Gruning et al. ................ 516/23
6,376,568 B1    4/2002  Baudin et al. .................. 522/6

FOREIGN PATENT DOCUMENTS

EP    1072326    1/2001
WO    02/14439    2/2002

OTHER PUBLICATIONS

Derwent Abstr. 1992-361390 [44] for JP 4262794 (1992).

R. Tor et al., Enzyme Microb. Technol., (1990), vol. 12, pp. 299-304.
W. Shi et al., Journal of Applied Polymer Science, vol. 59, No. 12, (1996), pp. 1937-1944.

*Primary Examiner*—Elvis O. Price
(74) *Attorney, Agent, or Firm*—Tyler A. Stevenson

(57) ABSTRACT

The invention relates to a process for preparing organosilicon group containing photoinitiators of the formula (I), wherein m is a number from 1 to 200; q is 0 or 1; A is IN-C(O)—O—$CHR_3$—Y— or IN-C(O)—NH—$CHR_3$—Y—; A' is A or $R_1$'; $R_1$ and $R_1$', $R_2$ and $R_2$' are $C_1$–$C_{18}$alkyl or phenyl, or —(O)$_q$—$SiR_1R_1'R_2$; $R_3$ is hydrogen or $C_1$–$C_6$alkyl, Y is a divalent group selected from $C_1$–$C_{10}$alkeylene, $C_2$–$C_{10}$alkenylene or —(CH$_2$)$_b$—O—(CH$_2$)$_a$—; and b are each independently of the other a number of 1 to 6; IN is a photolabile functional moiety of the formula (II) or (III), wherein $R_4$ is hydrogen or —C(O)—C(O)—OH or —C(O)—C(O)—O$C_1$–$C_6$alkyl and n is 1–3; $R_5$ and $R_6$ are $C_1$–$C_{12}$alkyl or together are cyclo$C_5$–$C_7$alkyl; $R_7$ is hydroxy, $C_1$–$C_6$alkoxy or morpholinyl; X is —(CH$_2$)$_a$—, —(CH$_2$)$_b$—O—(CH$_2$)$_a$— or —(CH$_2$)$_b$—O—CO—(CH$_2$)$_a$—; a and b are each independently of the other a number of 1 to 6; whereby the process is characterized in that a photolabile functional moiety containing a carboxy group (IN-COOH) or an alkoxycarbonyl group (IN-CO—O$C_1$–$C_6$alkyl) is reacted with a carbinol- or amino terminated organosilicon compound of the formula (IV), wherein m, $R_1$ and $R_1$', $R_2$ and $R_2$' are as defined above and B is —Y—$CHR_3$—OH or —Y—$CHR_3$—$NH_2$; B' is B or $R_1$', in the presence of an enzyme which catalyzes the esterification, transesterification or amidation reaction.

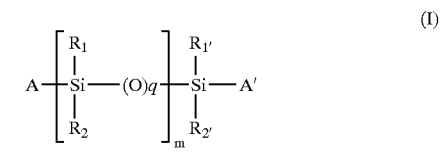

(I)

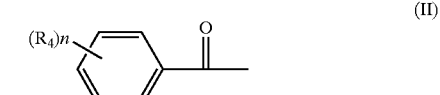

(II)

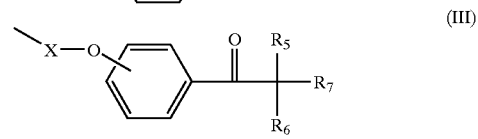

(III)

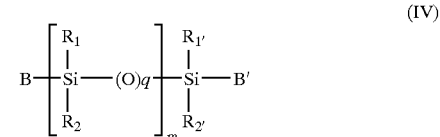

(IV)

12 Claims, No Drawings

ENZYMATIC PROCESS FOR PREPARING ORGANOSILICON GROUP CONTAINING PHOTOINITIATORS

The present invention relates to a novel process for preparing organosilicon group containing photoinitiators by esterifying or transesterifying or by amidation of carboxylic acids or carboxylates containing a photolabile functional group with a carbinol terminated organosilicon compound in the presence of an enzyme, which catalyzes the esterification or transesterification reaction.

U.S. Pat. No. 6,288,129 describes a process for esterifying or transesterifying acrylic acid and/or methacrylic acid or acrylic esters and/or methacrylic esters with hydroxy-functional and/or polyoxyalkylene-modified siloxane derivatives.

Organosilicon group containing photoinitiators may be obtained in a variety of ways. For example, they may be prepared by reacting a photoinitiator with at least one alkenyl radical and a siloxane in the presence of a platinum or rhodium catalysts as described, for example in U.S. Pat. No. 4,507,187.

The European Patent Publication EP-A 1072 326 describes, for example, the reaction of 2-hydroxy-2-methyl-1-[4-(2-propenyloxy)phenyl]-1-propanone with 1,1,1,3,5,5,5-heptamethyltrisiloxane in the presence of a platinum catalyst.

The International Application PCT/EP/01/09123 (WO 02/14439) describes, for example, the reaction of 2-allyloxyethyl glyoxalate with 1,1,1,3,5,5,5-heptamethyltrisiloxane in the presence of a platinum catalyst.

The siloxane molecule is thermally instable and, on being exposed to an elevated temperature, siloxane fragments may be obtained. Thus, the above mentioned synthesis process generally results in undesirable byproducts which are impurities, requiring a further purification such as, for example, purification by chromatography.

The problem to be solved is to provide a process for preparing organosilicon group containing photoinitiators having no impurities or less than those prepared by conventional processes.

It has now been found that the problem can be solved using an enzymatic synthesis process.

Thus, the present invention relates to a process for preparing organosilicon group containing photoinitiators of the formula I

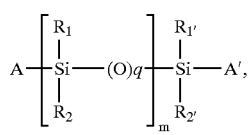

wherein
m is a number from 1 to 200;
q is 0 or 1;
A is IN-C(O)—O—CHR$_3$—Y— or IN-C(O)—NH—CHR$_3$—Y—;
A' is A or R$_1$';
R$_1$ and R$_1$', R$_2$ and R$_2$' independently of one another are C$_1$–C$_{18}$alkyl or phenyl, or —(O)$_q$—SiR$_1$R$_1$'R$_2$;
R$_3$ is hydrogen or C$_1$–C$_6$alkyl,
Y is a divalent group selected from C$_1$–C$_{10}$alkylene, C$_2$–C$_{10}$alkenylene or —(CH$_2$)$_b$—O—(CH$_2$)$_a$—; a and b are each independently of the other a number of 1 to 6;
IN is a photolabile functional moiety of the formula II or III

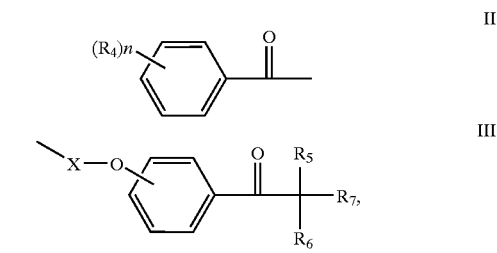

R$_4$ is hydrogen or —C(O)—C(O)—OH or —C(O)—C(O)—OC$_1$–C$_6$alkyl and n is 1–3;
R$_5$ and R$_6$ are C$_1$–C$_{12}$alkyl or together are cycloC$_5$–C$_7$alkyl;
R$_7$ is hydroxy, C$_1$–C$_6$alkoxy or morpholinyl;
X is —(CH$_2$)$_a$—, —(CH$_2$)$_b$—O—(CH$_2$)$_a$— or —(CH$_2$)$_b$—O—CO—(CH$_2$)$_a$—; a and b are each independently of the other a number of 1 to 6;

whereby the process is characterized in that a photolabile functional moiety containing a carboxy group (IN-COOH) or an alkoxycarbonyl group (IN-CO—OC$_1$–C$_6$alkyl) is reacted with a carbinol- or amino terminated organosilicon compound of the formula IV

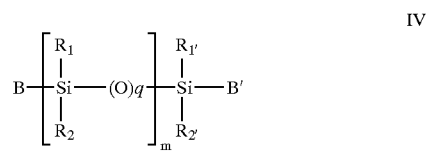

wherein m, R$_1$ and R$_1$', R$_2$ and R$_2$' are as defined above and
B is —Y—CHR$_3$—OH or —Y—CHR$_3$—NH$_2$;
B' is B or R$_1$', in the presence of an enzyme which catalyzes the esterification, transesterification or amidation reaction.

Preferred is a process for preparing organosilicon group containing photoinitiators of the formula I, wherein
m is a number from 1 to 20;
q is 0 or 1;
A is a group of the formula IIa or IIb

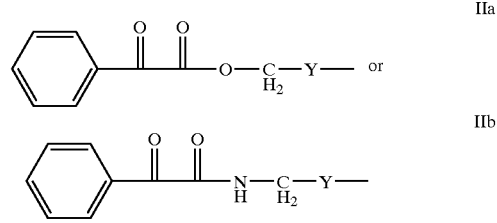

A' is A or R$_1$';
R$_1$ and R$_1$', R$_2$ and R$_2$' independently of one another are methyl, —O—Si(CH$_3$)$_3$ or —Si(CH$_3$)$_3$;
Y is a divalent group selected from C$_1$–C$_{10}$alkylene, C$_2$–C$_{10}$alkenylene or —(CH$_2$)$_b$—O—(CH$_2$)$_a$—; a and b are each independently of the other a number of 1 to 6;

whereby the process is characterized in that a photolabile functional moiety containing a carboxy group (IN-COOH) or an alkoxycarbonyl group (IN-CO—OC$_1$–C$_6$alkyl) is reacted with a carbinol- or amino terminated organosilicon compound of the formula IV $$\left[ B-\underset{\underset{R_2}{|}}{\overset{\overset{R_1}{|}}{Si}}-(O)_q \right]_m \underset{\underset{R_{2'}}{|}}{\overset{\overset{R_{1'}}{|}}{Si}}-B' \quad \text{IV}$$

wherein m, R$_1$ and R$_1$', R$_2$ and R$_2$' are as defined above and B is —Y—CH$_2$—OH or —Y—CH$_2$—NH$_2$;
B' is B or R$_1$', in the presence of an enzyme selected from esterases, lipases or proteases.

Preferred is also a process for preparing organosilicon group containing photoinitiators of the formula I, wherein
m is a number from 1 to 20;
q is 0 or 1;
A is a group of the formula IIIa or IIIb IIIa HO—C(CH$_3$)$_2$—C(=O)—[phenyl]—O—X—C(=O)—O—CH$_2$—Y— or IIIb HO—C(CH$_3$)$_2$—C(=O)—[phenyl]—O—X—C(=O)—NH—CH$_2$—Y—

A' is A or R$_1$';
R$_1$ and R$_1$', R$_2$ and R$_2$' independently of one another are methyl, —O—Si(CH$_3$)$_3$ or —Si(CH$_3$)$_3$;
Y is a divalent group selected from C$_1$–C$_{10}$alkylene, C$_2$–C$_{10}$alkenylene or —(CH$_2$)$_b$—O—(CH$_2$)$_a$—; a and b are each independently of the other a number of 1 to 6;
X is —(CH$_2$)$_a$—, —(CH$_2$)$_b$—O—(CH$_2$)$_a$— or —(CH$_2$)$_b$—O—CO—(CH$_2$)$_a$—; a and b are each independently of the other a number of 1 to 6;

whereby the process is characterized in that a photolabile functional moiety containing a carboxy group (IN-COOH) or an alkoxycarbonyl group (IN-CO—OC$_1$–C$_6$alkyl) is reacted with a carbinol- or amino terminated organosilicon compound of the formula IV $$\left[ B-\underset{\underset{R_2}{|}}{\overset{\overset{R_1}{|}}{Si}}-(O)_q \right]_m \underset{\underset{R_{2'}}{|}}{\overset{\overset{R_{1'}}{|}}{Si}}-B' \quad \text{IV}$$

wherein m, R$_1$ and R$_1$', R$_2$ and R$_2$' are as defined above and B is —Y—CH$_2$—OH or —Y—CH$_2$—NH$_2$;
B' is B or R$_1$', in the presence of an enzyme selected from esterases, lipases or proteases.

Definitions, Preferences and Avaibility.

Siloxane Moiety

The term "silanes" refers in this context to oligomers or polymers having a main chain of —Si—Si— whereas the term "siloxanes" refers to oligomers and polymers having a main chain of —Si—O—Si—.

Preferred are siloxanes having 2–20 Si-units, more preferably 2–10 Si-units.

The residues R$_1$ and R$_1$', R$_2$ and R$_2$' are preferably methyl, —O—Si(CH$_3$)$_3$ or —Si(CH$_3$)$_3$.

C$_1$–C$_{18}$Alkyl is linear or branched and is for example C$_1$–C$_{12}$–, C$_1$–C$_8$—, C$_1$–C$_6$— or C$_1$–C$_4$alkyl. Examples are methyl, ethyl, propyl, isopropyl, n-butyl, sec-butyl, iso-butyl, tert-butyl, pentyl, hexyl, heptyl, 2,4,4-trimethyl-pentyl, 2-ethylhexyl, octyl, nonyl, decyl, undecyl, dodecyl, tetradecyl, pentadecyl, hexadecyl, heptadecyl or octadecyl.

C$_1$–C$_{12}$Alkyl, C$_1$–C$_8$alkyl and C$_1$–C$_4$alkyl have the same definitions as indicated above but with the corresponding number of carbon atoms.

C$_1$–C$_{10}$Alkylene Y is linear or branched alkylene, for example C$_1$–C$_8$—, C$_1$–C$_6$—, C$_1$–C$_4$—, C$_2$–C$_8$—, C$_2$–C$_4$alkylene, such as methylene, ethylene, propylene, isopropylene, n-butylene, sec-butylene, iso-butylene, tert-butylene, pentylene, hexylene, heptylene, octylene, nonylene or decylene.

In particular, Y is C$_1$–C$_8$alkylene, for example ethylene, propylene, hexylene, octylene,

—CH(C$_7$H$_{15}$)—,  —CH(CH$_3$)—CH$_2$—,  —CH(CH$_3$)—(CH$_2$)$_2$—,

—CH(CH$_3$)—(CH$_2$)$_3$—,  —C(CH$_3$)$_2$—CH$_2$— or

—CH$_2$—C(C$_2$H$_5$)(CH$_3$)—CH$_2$—.

C$_2$–C$_{10}$Alkenylene is mono- or polyunsaturated, linear or branched and is for example C$_2$–C$_8$—, C$_3$–C$_6$—, C$_2$–C$_4$alkenylene, for example ethenylene, 1-propenylene, 1-butenylene, 3-butenylene, 2-butenylene, 1,3-pentadienylene, 5-hexenylene or 7-octenylene.

The linker group Y may also be a trivalent group such as for example

—(CH$_2$)$_a$—CH((CH$_2$)$_c$)—(CH$_2$)$_b$—   or   —(CH$_2$)$_a$—CH(O—(CH$_2$)$_c$)—(CH$_2$)$_b$—

Trivalent linker groups enable functionalization with two photoinitiator moieties on the same Si-unit.

Some of the carbinol terminated siloxanes of the fomula IV are commercially available, for example from the company Th. Goldschmidt, Essen as Tegomer H—Si 2111; from Witco Corporation as L-7608; from Dow Corning, Midland, Mich., USA under the Q, e.g., QS-5211 product line or from Rhone Poulenc as Rhodorsil 1647 V60.

The carbinol terminated siloxanes may be obtained by methods known to the person skilled in the art, for example by hydrosilylation of an organosilicon compound containing Si-bonded hydrogen (Si—H-group) with an alkene having a hydroxyalkyl functional group such as for example HO—CH$_2$—CH=CH$_2$ in the presence of a platinum catalyst. Such methods are described, for example in EP-A-612759 corresponding to U.S. Pat. No. 5,831,080.

The preparation of siloxanes containing hydroxyalkyl groups is also described by K. Tamao et al. Organometallics 1983, 2, 1694.

Some of the amino terminated organosiloxanes are commercially available from ABCR GmbH and Co, Karlsruhe, Germany. Further preparation methods and literature references for preparation can be found in the catalogue of the Geleste company, "ABCR Geleste 2000".

Furthermore, the preparation of the aminoterminated organosiloxanes can be done as described by N. Sabourault et al in Organic letters 2002, 4, 2117 by hydrosilylation of an aminated alkene using platinum oxide.

The preparation of the silanes is described, for example, by B. Kopping et al. J. Org. Chem. 1992, 57, 3994.

Photoinitiator Moiety

In one aspect of the invention the photolabile moiety is derived from arylglyoxalates, especially phenylglyoxalates as described in the PCT-Publication WO02/14439 (PCT/EP/01/09123).

It is of course also possible to use naphthyl- or anthracenyl-glyoxalates or substituted phenylglyoxalates as described in PCT-Publication WO02/14439 (PCT/EP/01/09123). Substituents are, for example, unsubstituted $C_1$–$C_{12}$alkyl or $C_1$–$C_{12}$alkyl substituted by OH, $C_1$–$C_4$alkoxy, phenyl, naphthyl, halogen, CN and/or —O(CO)$C_1$–$C_8$alkyl or —O(CO)phenyl; or are $C_2$–$C_{12}$alkyl interrupted by one or more non-successive oxygen atoms; or are $C_1$–$C_{12}$alkoxy; $C_1$–$C_{12}$alkylthio, $C_1$–$C_{12}$alkylamino, di$C_1$–$C_{12}$alkylamino; halogen; unsubstituted or $C_1$–$C_4$alkyl- and/or $C_1$–$C_4$alkoxy-substituted phenyl or are groups —C(O)—C(O)—OH or —C(O)—C(O)—O—$C_1$–$C_6$alkyl. If the photolabile moiety "IN" is derived from p-phenylene diglycolic acid, it goes without saying that two carbinol terminated organosilicon compounds may be bound.

However, unsubstituted phenylglyoxalates are preferred.

Some of the phenylglyoxalates are commercially available, for example methyl phenylglyoxylate also known as Genocure MBF, available from Rahn, Inc.

In another aspect of the invention the photolabile moiety is derived from alpha hydroxy- or amino ketones as described in the European Patent Publication EP-A 1072 326. It is of course also possible to use phenyl substituted alpha hydroxy- or amino ketones wherein possible substituents are the ones listed above.

Enzymes

Enzymes which can be employed in the present invention as catalysts are hydrolases, especially esterases, lipases and proteases as described in U. T. Bornscheuer, R. T. Kazlauskas in: Hydrolases in Organic Synthesis; Wiley-VCH, 1999, Seite 65–195, ISBN 3-527-30104-6).

Specific examples of esterases are those obtained from animals such as horse liver esterase, pig liver esterase, pig pancreas esterase, fungal esterases or esterases from microorganisms such as from *Bacillus subtilis* or from *Pichia polimorpha; Rhizopus* sp.-esterases, *Penicillium* sp.-esterases or yeast esterases or from *Candida* species, *Alcaligene* species or *Pseudomonas* species.

Lipases suitable for use herein include those of animal, plant and microbiological origin.

Suitable lipases are also found in many strains of bacteria and fungi.

Specific examples are porcine pancreatic lipase (PPL), (*G. candidum* (GCL), *H. lanuginosa* (HLL). *Rhizopus* sp. (RML, ROL), *Candida* sp. (CAL-A, CAL-B, CCL), *Aspergillus* sp. (ANL), *Pseudomonas* sp. (PCL, PFL) *Burholderia* sp. (lipase QLM)

Examples of suitable proteolytic enzymes are the subtilisins, thermitase, chymotrypsin, thermolysin, papain, aminoacylasen, penicillin amidases or trypsin. Suitable enzymes are known to those skilled in the art and are not limited to the ones mentioned above.

The enzymes can be employed as crude extracts, in pure form or in immobilized form crude or pure, on a support on which they are bound chemically or physically.

Suitable supports are for example silica gel, diatomite, polyacrylamide, Duolite®, Celite®, Eupergit® (Röhm&Haas, Darmstadt, Deutschland) and the like.

The enzymes can also be employed as cross-linked-enzymes (CLEC's), which enzymes may be obtained from Altus Corp. Suitable enzyme employments are well known and are described, for example, in U. T. Bornscheuer, R. T. Kazlauskas in: Hydrolases in Organic Synthesis; Wiley-VCH, 1999, Site 61–64, ISBN 3-527-30104-6, K. Faber in: Biotransformation in Organic Chemistry, Springer 1997, $3^{rd}$ Ed., 345–357, ISBN 3-540-61688-8; H.-J. Rehm, G. Reed In Biotechnology, VCH 1998, $2^{nd}$, Ed. 407–411.

Preferred are enzymes that are commercially available (Fluka, Sigma, Novo, Amano, Roche etc) or enzymes that are well known and described, for example, by H.-J. Rehm, G. Reed In Biotechnology, VCH 1998, $2^{nd}$, Ed. page 40–42).

Especially preferred are immobilized lipases, that are thermostable such as Novozyme 435 (recombinante *Candida antarctica* lipase B (E. M. Anderson et al. Biocat. Biotransf. 1998, 16, 181), (Firma NOVO Nordisk, Bagswaerd, Dänemark)) or the enzyme QLM, QL (Meito Sangyo, Japan).

Enzymes having esterase, lipase and/or protease activity may be obtained from natural sources and/or from microorganism using standard procedures known in the art, for example from cloning processes via expression and amplification.

Process Parameters

The enzymatic esterification, transesterification or amidation is carried out at low temperatures, especially from 10–100° C., preferably from 25–75° C.

The enzymatic esterification, transesterification or amidation can be carried out without adding a solvent or in organic solvents such as for example in hexane, toluene, benzene, THF, diethyl ether, methyl-t.butyl ether, methylene chloride and the like.

The amount of the enzyme catalyst depends on the substrate used and on the reaction conditions such as temperature, reaction time, solvent but may be from 0.01 to 20% by weight, preferably from 1 to 10% by weight based on the modified siloxane employed.

The reaction time depends on the amount used and on the activity of the enzyme catalyst, and is, for example, up to 48 hours, preferably up to 24 hours.

In order to maximize the degree of conversion, it is advantageous to remove the water and/or alkanol of reaction, for example by vacuum distillation.

After the end of reaction, the enzyme catalyst can be separated off by means of appropriate measures, such as filtration or decantation, and can, if desired, be used any number of times.

It is advantageous to use immobilized or unsoluble enzymes. Such methods are described in general by W. Tischer et al. TIBTECH 1999, 17, 326; J. Lalonde, Curr. Opin. Drug Disc. & Develop. 1998, 1(3), 271.

It is also possible to carrying out the process continuously in an appropriate reactor. Such processes are described in general in V. M. Balcao et al. Enzyme Microbiol. Techn. 1996, 18, 392; L. Giorno et al. TIBTECH 2000, 18, 339.

Most preferred is a process wherein the immobilized enzyme is packed in a column and the reactants are passed through with or without solvent in an appropriate vacuum to remove side products until the desired transformation is achieve (continuous loap reactor).

Advantage

Enzymatic processes operate under mild conditions such as low temperatures and under neutral pH conditions. Thus, less byproducts are produced in the inventive process. The enzyme catalyst can be easily separated off as it is not soluble in the organic solvents used. Most advantageously the enzymatic process may also be carried out continuously.

The enzymatic (trans)esterification or amidation is not limited to photoinitiators having an α-ketocarboxylic acid or ester group. It goes without saying that α-ketocarboxylic acids or esters in general may be used for the (trans) esterification or amidation reaction.

The following examples are given to illustrate the present invention.

EXAMPLE 1

Preparation of

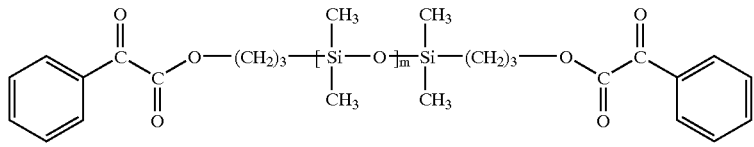

$q=1$, $m=11$, $A=A'=IN-C(O)-O-CH_2-Y-$; IN is Phenyl-CO—, $Y=-(CH_2)_2-$, $R_1=R_1'=R_2=R_2'=CH_3$, $R_4$ is H.

Two equivalents (1.00 g) methyl phenylglyoxalate and 1 equivalent (3.20 g) of siloxanol of the formula

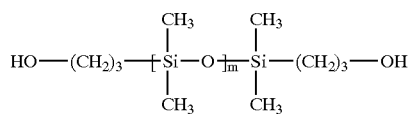

are dissolved in 3 ml toluene at room temperature until a clear solution is obtained. 1.00 g of enzyme (Novozym® 435) is added. The reaction tube is placed into a waterbath at 50° C. and the reaction mixture is slowly stirred at 50° C. under low pressure (250 Torr). When the reaction is complete (results of proton NMR indicated complete reaction) the reaction mixture is diluted with toluene (or another suitable solvent such as, for example ethyl acetate, acetone or methylene chloride). The reaction mixture is filtered to remove the biocatalyst and the solvent is evaporated. If appropriate a filtration over Acrodisc® (CR PTFE, 0.45 μm) may follow to remove clouding materials.

Yield: 3.60 g (94%) of the above product.

The recovered biocatalyst can be re-used in later reactions.

$^1$H-NMR in ppm (CDCl$_3$, 200 MHz): 0.00–0.06 m (~77 H); 0.52–0.59 m (4H); 1.69–1.81 m(4 H); 4.28 t (J=7.0 Hz, 4 H); 7.40–7.53 m (4 H); 7.55–7.61 m (2 H); 7.90–7.93 m(4 H). $^{13}$C-NMR in ppm (CDCl$_3$, 50 MHz): 0.96; 1.06; 13.87; 22.44; 68.42; 128.56; 129.69; 132.27; 134.50; 163.58; 186.05. $^{28}$Si-NMR in ppm (CDCl$_3$, 100 MHz): −21.9; 7.5.

EXAMPLE 2

Preparation of

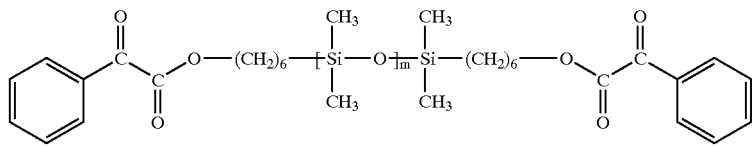

$q=1$, $m=7.3$, $A=A'=IN-C(O)-O-CH_2-Y-$; IN is Phenyl-CO—, $Y=-(CH_2)_5-$, $R_1=R_1'=R_2=R_2'=CH_3$, $R_4$ is H.

Two equivalents (0.50 g) methyl phenylglyoxalate and 1 equivalent (1.22 g) of siloxanol of the formula

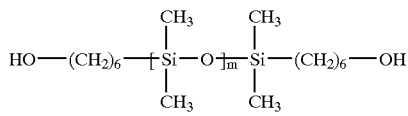

are dissolved in 5 ml toluene at room temperature until a clear solution is obtained. 0.259 of enzyme (Novozym® 435) is added. The reaction is carried out analogue to Example 1 under 150 Torr vacuum Yield: 33 g (82%) of the above product. $^1$H-NMR in ppm (CDCl$_3$, 200 MHz): 0.01–0.04 m (~48 H); 0.52–0.59 m (4 H); 1.26–1.43 m (12H); 1.69–1.75 m (4 H); 4.34 t (J=7.0 Hz, 4 H); 7.42–7.49 m (4 H); 7.57–7.63 m(2 H); 7.94–7.96 m(4 H). $^{28}$Si-NMR in ppm (CDCl$_3$, 100 MHz): −22.4; −21.9; −21.6; 7.6.

Analogue May be Prepared

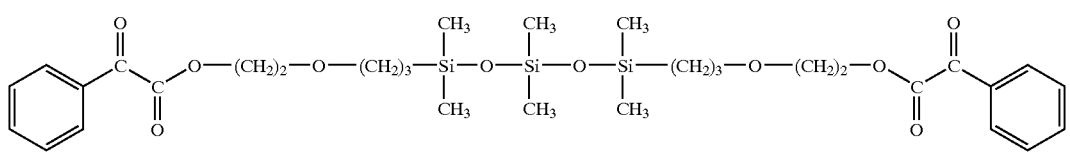

EXAMPLE 3

Preparation of

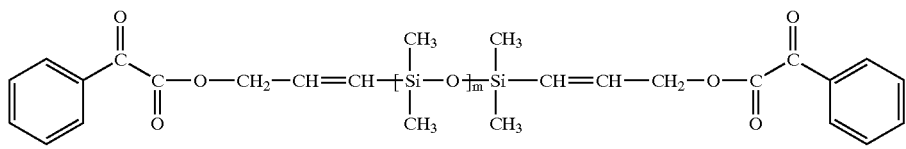

q=1, m=9, A=A'=IN-C(O)—O—CH$_2$—Y—; IN is Phenyl-CO—, Y=—CH=CH—, R$_1$=R$_1$'=R$_2$'=CH$_3$ R$_4$ is H. 5.00 g of enzyme (Novozym® 435) is added to a mixture of two equivalents (7.00 g) methyl phenylglyoxalate and one equivalent (20.0 g) of siloxanol of the formula

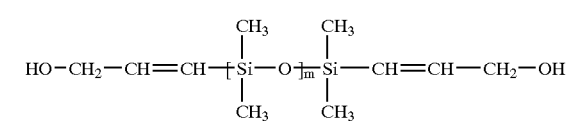

The reaction is carried out analogue to Example 1.

Yield: 25.4 g (99%) of the above product. $^1$H-NMR in ppm (CDCl$_3$, 200 MHz): 0.00–0.04 m (~60 H); 3.48–3.80 m (8.1 H); 3.90–3.92 m (1 H); 3.98–4.12 m (4.8 H); 4.47–4.54 m (3.3 H); 5.46–6.14 m (3.9 H); 7.38–7.47 m (4 H); 7.54–7.61 m (2 H); 7.92–7.95 m (4 H). $^{13}$C-NMR in ppm (CDCl$_3$, 50 MHz): diagnostic signals: −0.44; 0.14; 7.49; 127.72; 133.81; 141.23; 146.70; 162.61; 184.97. $^{28}$Si-NMR in ppm (CDCl$_3$, 99.3 MHz): −3.5; −4.1; −20.8; −20.9; −21.9

EXAMPLE 4

Preparation of

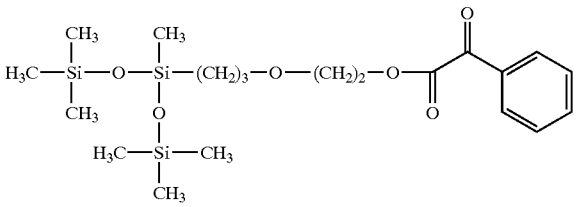

q is 1; m=1, A=IN-C(O)—O—CH$_2$—Y—, IN is Phenyl-CO—, Y=—(CH$_3$)$_3$—O—(CH$_2$)—, R$_1$=CH$_3$, R$_1$', R$_2$' und A'=CH$_3$, R$_2$=O—Si(CH$_3$)$_3$, R$_4$ is H. 1.50 g of enzyme (Novozym® 435) is added to a mixture of two equivalents (2.50 g) methyl phenylglyoxalate and one equivalent (5.0 g) of siloxanol of the formula

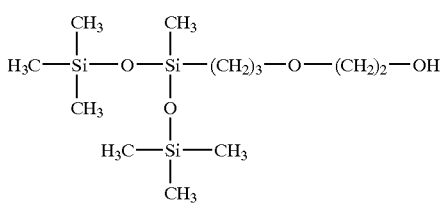

The reaction is carried out analogue to Example 1. When the reaction is complete, the reaction mixture is diluted with methylene chloride.

Yield: 6.30 g (94%) of the above product. $^1$H-NMR in ppm (CDCl$_3$, 200 MHz): 0.00 s (3 H); 0.07 s (18 H); 0.42–0.49 m (2 H); 1.56–1.67 m (2 H); 3.44 t (J=7.0 Hz, 2 H); 3.72–3.76 m (2 H); 4.51–4.55 m (2 H). 7.44–7.51 m (2 H); 7.58–7.65 m (1 H); 7.98–8.02 m (2 H). $^{13}$C-NMR in ppm (CDCl$_3$, 50 MHz): −0.265; 1.93; 13.57; 23.30; 64.97; 67.98; 74.04; 128.72; 129.97; 132.38; 134.71; 163.66; 186.01. $^{28}$Si-NMR in ppm (CDCl$_3$, 99.3 MHz): 7.3, −21.8

The above siloxanol is prepared according to K. Tamao et al. Organometallics 1983, 2. 5.00 g 2-allyloxyethanol (Aldrich) are heated to 80° C. under argon. 50 µl of a solution of 0.1 g of hexachloroplatinic acid in 9.9 ml 2-propanol is added. 19.20 ml 1,1,1,3,5,5,5-heptamethyltrisiloxan (Aldrich) are added within 20 minutes. The temperature of the reaction mixture is kept at 80° C. until the reaction is completed. 11.80 g (75%) of the above siloxanol is obtained by fractional distillation under high vacuum. (0.08 mbar, 115° C.).

$^1$H-NMR in ppm (CDCl$_3$, 200 MHz): 0.00 s (3 H); 0.07 s (18 H); 0.41–0.47 m (2 H); 1.54–1.66 m (2 H); 2.33 breit (OH); 3.41 t (J=7.0 Hz, 2 H); 3.48–3.53 m (2 H); 3.68–3.72 m (2 H). $^{13}$C-NMR in ppm (CDCl$_3$, 50 MHz): −0.276; 1.92; 13.63; 23.31; 61.80; 71.68; 73.87. $^{28}$Si-NMR in ppm (CDCl$_3$, 99.3 MHz): 7.3, −21.8

Analogues may be obtained.

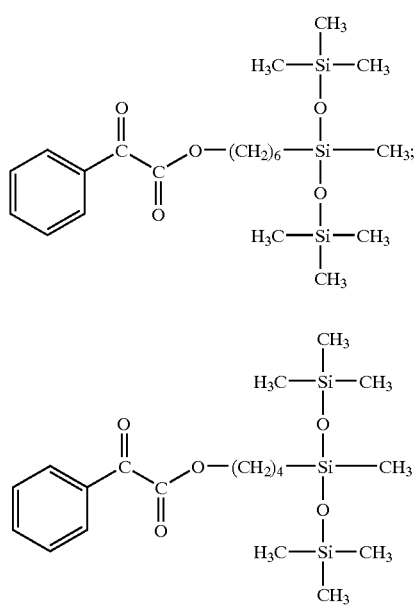

The photoinitiators as described in the International Application PCT/EP/01/09123 may be prepared analogously.

EXAMPLE 5

Preparation of

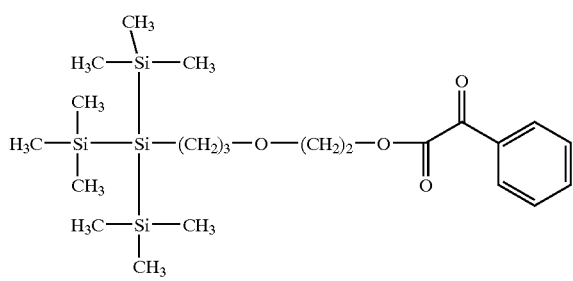

q=0; m=1, A=IN-C(O)—O—CH$_2$—Y—, IN is Phenyl-CO—, Y=—(CH$_2$)$_3$—O—(CH$_2$)—, R$_1$=R$_2$=—Si(CH$_3$)$_3$, R$_1$', R$_2$' und A'=CH$_3$, R$_4$ is H.

1.10 g of enzyme (Novozym® 435) is added to a mixture of 2 equivalents (1.40 g) methyl phenylglyoxalate and 1 equivalent (3.00 g) of organosilicon compound of the formula

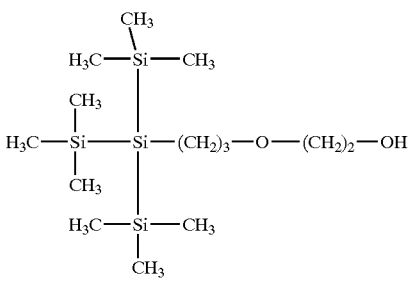

The reaction tube is placed into a waterbath at 50° C. and the reaction mixture is slowly stirred at 50° C. under low pressure (250 Torr). When the reaction is complete (results of proton NMR indicated complete reaction) the reaction mixture is diluted with acetone. The reaction mixture is filtered to remove the biocatalyst and the solvent is evaporated. If appropriate a filtration over Acrodisc® (CR PTFE, 0.45 µm) may follow to remove clouding materials.

Yield: 3.25 g (79%) of the above product.

The recovered biocatalyst can be re-used in later reactions.

$^1$H-NMR in ppm (CDCl$_3$, 200 MHz): 0.00 s (27 H); 0.57–0.64 m (2 H); 1.46–1.57 m (2 H); 3.29 t (2 H, J=6.7 Hz); 3.58–3.62 m (2 H); 4.36–4.40 m (2 H); 7.30–7.36 m (2 H); 7.44–7.51 m (1 H); 7.82–7.88 m (2 H). $^{13}$C-NMR in ppm (CDCl$_3$, 50 MHz): 1.21; 27.55; 64.93; 67.96; 74.44; 128.93; 129.93; 132.28; 134.81; 163.58; 185.93. $^{28}$Si-NMR in ppm (CDCl$_3$, 99.3 MHz): −12.8, −81.3

The organosilicon product is prepared according to B. Kopping et al. J. Org. Chem. 1992, 57, 3994. 4.00 ml tris(trimethylsilyl)silane (Fluka) and 1.10 g allyloxyethanol (Aldrich) are dissolved in 80 ml under argon atmosphere. 0.44 g azo-isobutyronitril (Fluka) is added. The reaction mixture is heated to 90° C. The temperature of the reaction mixture is kept at 90° C. until the reaction is completed. 3.30 g (70%) of the above organosilicon-compound is obtained by fractional distillation under high vacuum (0.10 mbar, 100° C.).

$^1$H-NMR in ppm (CDCl$_3$, 200 MHz): 0.00 s (27 H); 0.56–0.62 m (2 H); 1.44–1.55 m (2 H); 1.95 breit (OH); 3.25 t (2 H, J=7.0 Hz); 3.36 t (2 H, J=4.4 Hz); 3.54–3.58 m (2 H). $^{13}$C-NMR in ppm (CDCl$_3$, 50 MHz): −0.76; 21.52; 27.02; 59.95; 69.82; 72.58. $^{28}$Si-NMR in ppm (CDC$_3$, 99.3 MHz): −12.8, −81.3

EXAMPLE 6

Preparation of

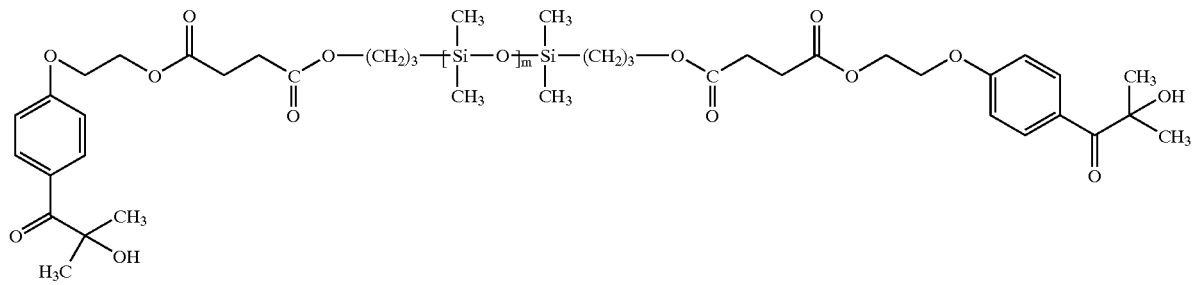

$q=1$, $m=11$, $A=A'=IN-C(O)—O—CH_2—Y$; IN is a group of the formula III with $R_5=R_6$=methyl, $R_7$=OH, X is —$(CH_2)_2$—O—CO—$(CH_2)_2$—, Y=—$(CH_2)_2$—, $R_1=R_2=R_1'=R_2'=CH_3$.

Two equivalents (50 mg) of succinic acid ethyl ester 2-[4-(2-hydroxy-2-methyl-propionyl)-phenoxy]-ethyl ester and 1 equivalent (76.6 mg) of siloxanol of the formula

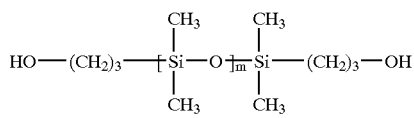

are added to 50 mg of enzyme (Novozym® 435) and the mixture is heated at 45 to 50° C. under a vacuum of 350 mbar for approximately 2 days. The mixture is taken up in toluene, the enzyme removed by filtration and the solvent subsequently removed in vacuo. A filtration over Acrodisc® (CR PTFE, 0.45 μm) may follow to remove clouding materials.

Yield: 92 mg (73%) of the above product. $^1$H-NMR in ppm (CDCl$_3$, 300 MHz): −0.01–0.05 (76 H); 0.42–0.55 (4 H); 1.55–1.65 (16 H); 2.56 (8 H); 4.05–4.20 (8 H); 4.41 (4 H); 6.90 (4 H); 8.00 (4 H). $C^{13}$—NMR in ppm (CDCl$_3$, 75 MHz): 0.0, 1.1, 13.9, 24.8, 28.6, 28.8, 28.9, 62.4, 62.5, 67.0, 67.1, 69.3, 75.7, 113.9, 114.5, 135.1, 132.1, 161.9, 171.8, 171.9, 202.2. 28 Si-NMR in ppm (CDCl3, 99.3 MHz): −21.8. −7.4

Succinic acid ethyl ester 2-[4-(2-hydroxy-2-methyl-propionyl)-phenoxy]-ethyl ester is prepared analoguous to the preparation described in the European Patent Publication EP-A-1072326 starting from 2-hydroxy-1-(4-hydroxyphenyl)-2-methyl-1-propanone.

EXAMPLE 7

Preparation of

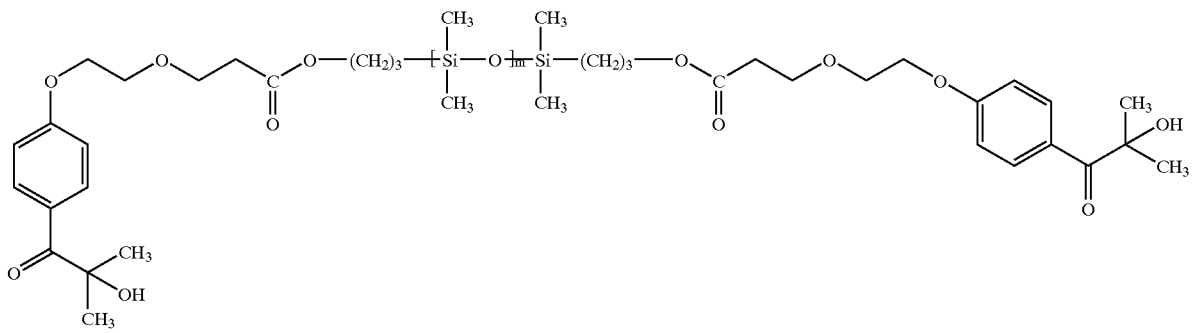

$q=1$, $m=11$, $A=A'=IN-C(O)—O—CH_2—Y$; IN is a group of the formula III with $R_5=R_6$=methyl, $R_7$=OH, X is —$(CH_2)_2$—O—$(CH_2)_2$—, Y=—$(CH_2)_2$—, $R_1=R_2=R_1'=R_2'=CH_3$, Two equivalents (50 mg) of 3-{2-[4-(2-Hydroxy-2-methyl-propionyl)-phenoxy]-ethoxy}-propionic acid ethyl ester and 1 equivalent (83 mg) of siloxanol of the formula

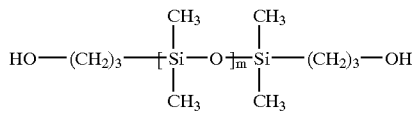

are dissolved in 2 ml toluene and 50 mg of enzyme (Novozym® 435) are added. The reaction vessel is cautiously evacuated (20–30 mbar) and after disappearal of the solvent the mixture is heated at 50–60° C. for 1 day. The mixture is taken up in toluene, the enzyme removed by filtration and the solvent subsequently removed in vacuo. A filtration over Acrodisc® (CR PTFE, 0.45 μm) may follow to remove clouding materials.

Yield: 114 mg (87%) of the above product. $^1$H-NMR in ppm (CDCl$_3$, 300 MHz): 0.00–0.04 (~77 H); 0.46 (4 H); 1.53–1.65 (16 H); 2.55–2.64 (4 H); 3.97 (4 H); 4.10 (4 H); 4.18 (4 H); 4.40 (4 H); 6.68–6.92 (4 H); 7.97 (4 H). C$^{13}$—NMR in ppm (CDCl$_3$, 75 MHz): 0.0, 1.0, 13.9, 22.4, 28.5, 28.8, 28.9, 29.0, 62.4, 65.8, 67.0, 69.3, 75.7, 113.9, 114.5, 127.5, 132.1, 161.9, 171.8, 171.9, 202.2. 28 Si-NMR in ppm (CDCl3, 99.3 MHz): −21.8. −7.4

EXAMPLE 8

Preparation of

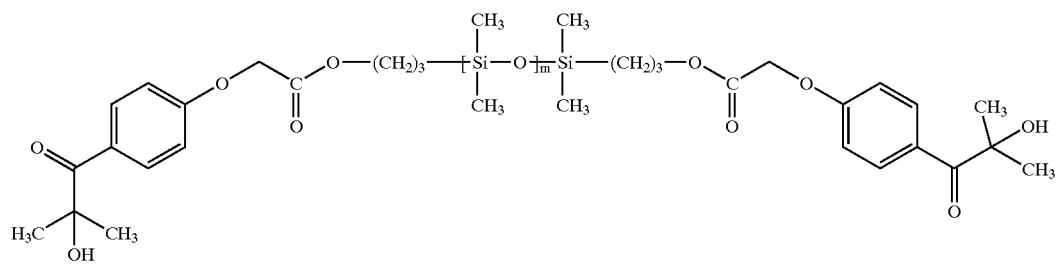

q=1, m=11, A=A'=IN-C(O)—O—CH$_2$—Y; IN is a group of the formula III with R$_5$=R$_6$=methyl, R$_7$=OH, X is —(CH$_2$)—, Y=—(CH$_2$)$_2$—, R$_1$=R$_2$=R$_1$'=R$_2$'=CH$_3$, Two equivalents (50 mg) of 3-{2-[4-(2-Hydroxy-2-methyl-propionyl)-phenoxy]-ethoxy}-propionic acid ethyl ester and 1 equivalent (76 mg) of siloxanol of the formula

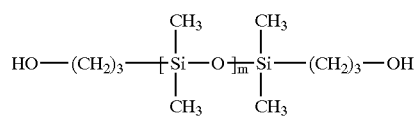

are dissolved in 2 ml toluene and 50 mg of enzyme (Novozym® 435) are added. The reaction vessel is cautiously evacuated (20–30 mbar) and after disappearal of the solvent the mixture is heated at 50–60° C. for 1 day. The mixture is taken up in toluene, the enzyme removed by filtration and the solvent subsequently removed in vacuo. A filtration over Acrodisc® (CR PTFE, 0.45 μm) may follow to remove clouding materials.

Yield: 102 mg (81%) of the above product. $^1$H-NMR in ppm (CDCl$_3$, 300 MHz): 0.02 (~76 H); 0.45–0.63 (4 H); 1.54–1.66 (16 H); 2.56 (4 H); 3–75–4.2 (8 H); 6.90 (4 H); 7.96 (4 H). C$^{13}$—NMR in ppm (CDCl$_3$, 75 MHz): −1.1, 1.0, 13.9, 22.5, 28.6, 34.9, 66.9, 67.2, 69.2, 75.6, 114.0, 114.5, 125.8, 126.9, 132.0, 162.3, 171.1, 202.1 28 Si-NMR in ppm (CDCl3, 99.3 MHz): −21.8. −7.4

EXAMPLE 9

Preparation of

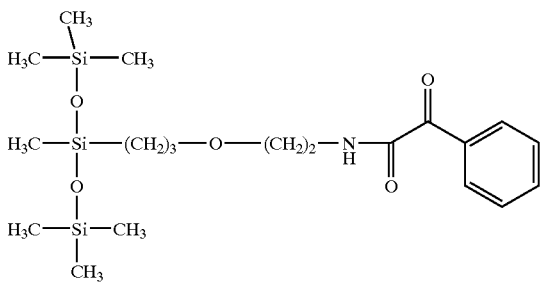

q=1; m=1, A=IN-C(O)—NH—CH$_2$—Y—, IN is Phenyl-CO—, Y=—(CH$_3$)$_3$—O—(CH$_2$)—, R$_1$', R$_2$' und A'=CH$_3$, R$_4$ is H, R$_1$=—O—Si(CH$_3$)$_3$, R$_2$=CH$_3$.

(In analogy of the exemplary paper: Z. Djeghaba et al. Tetrahedron Lett. 1991, 32(6). 761

Three equivalents (0.183 g) oxo-phenyl-acetic acid methyl ester and one equivalent (0.36 g) of amine of the following formula

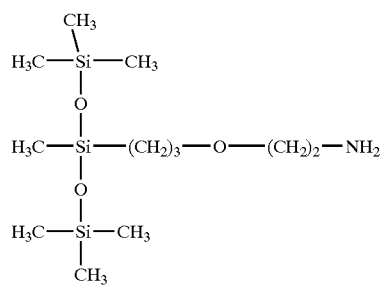

are dissolved in 10 mL diisopropylether. 2 g of enzyme (Novozym® 435) and 2 g molecular sieve (0.4 nm) are added and the reaction is stirred at 70° C. Total conversion is not achieved after 23 h (results of TLC), however, work up followed. The reaction mixture is filtered through a plug of celite to remove the biocatalyst and the solvent is evaporated. The residue is purified by flash chromatography (hexane/EtOAc, 4:1). Yield: 0.026 g, $R_f$ (hexane/EtOAc, 4:1)=0.75 $^1$H-NMR in ppm (CDCl$_3$, 300 MHz): δ=0.00 (3 H, s), 0.07 (18 H, s), 0.41–0.47 (2 H, m), 1.54–1.64 (2 H, m), 3.39 (2 H, t, J=6.7), 3.55 (4 H, d, J=2.6), 7.34 (1 H, bs), 7.40–7.46 (2 H, m) 7.54–7.61 (1 H, m), 8.26–8.28 (2 H, m); C$^{13}$—NMR (CDCl$_3$, 75 MHz): δ=0.0, 2.2, 13.9, 23.5, 39.7, 68.9, 74.1, 128.6, 131.3, 133.6, 134.4, 162.0, 187.7;

The above amine is prepared as follows:

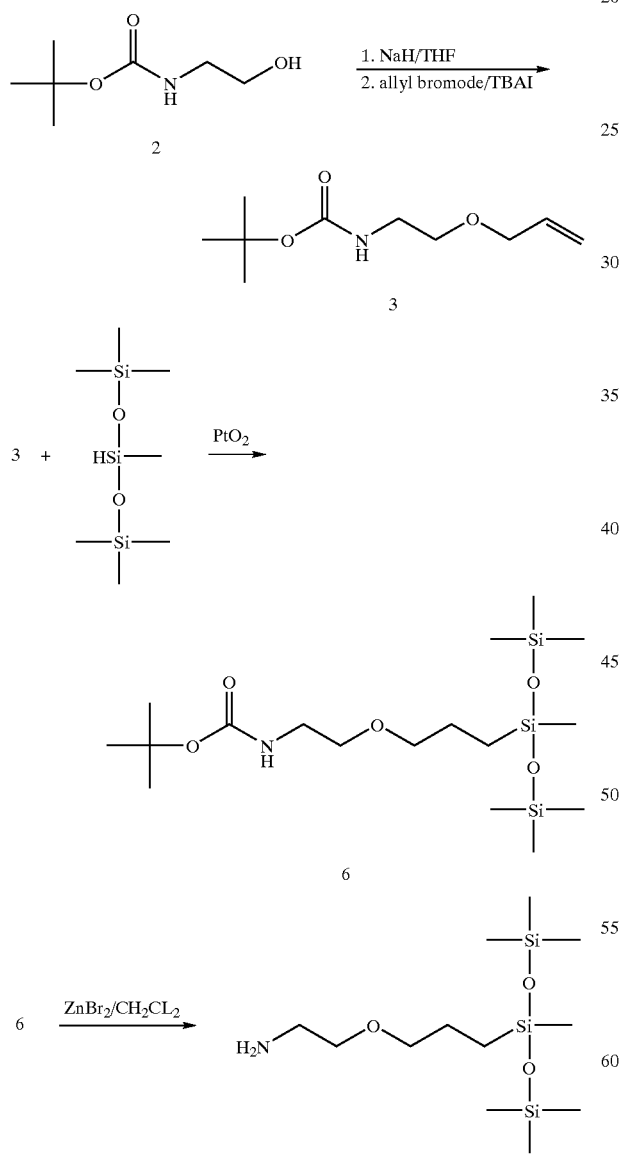

Siloxane 6 is prepared according to literature: N. Sabourault et al, Organic Letters, 2002, 4, 2117.

One equivalent (0.3 g) of compound 3, 1.4 equivalents (0.47 g) of siloxane 5 (Aldrich) and 2 mg of PtO$_2$ (Fluka) are stirred under inert gas atmosphere at 85° C. until full conversion.

The reaction mixture is directly purified by flash chromatography (hexane/EtOAc, 5:1) to yield siloxane 6. Yield: 2.66 g (71%).

$R_f$ (hexane/EtOAc, 2:1)=0.90 $^1$H-NMR in ppm (CDCl$_3$, 300 MHz): δ=0.00 (3H, s), 0.07 (18H, s), 0.40–0.46 (2H, m), 1.43 (9H, s), 1.52–1.61 (2H, m), 3.24–3.31 (2H, m), 3.35 (2H, t, J=6.7), 3.44 (2H, t, J=5.0), 5.86 (1H, bs); C$^{13}$—NMR (CDCl$_3$, 75 MHz): δ=0.0, 2.2, 13.9, 23.6, 28.7, 40.5, 69.8, 74.0, 79.8, 156.2.

One equivalent of siloxane 6 (1.73 g) and 2.7 equivalents ZnBr$_2$ are dissolved in 30 mL CH$_2$Cl$_2$. The reaction is stirred at room temperature until completion (results of TLC).

The reaction mixture is filtered through a plug of celite and the solvent is evaporated.

The residue is purified by flash chromatography (CH$_2$Cl$_2$/MeOH, 10:1) to afford amine 4.

Yield 1.19 g $R_f$ (CH$_2$Cl$_2$/MeOH, 10:1)=0.70 $^1$H-NMR in ppm (CDCl$_3$, 300 MHz): δ=0.00 (3H, s), 0.07 (18H, s), 0.37–0.44 (2H, m), 1.51–1.63 (2H, m), 3.37 (2H, t, J=2.5), 3.44 (2H, t, J=7.0), 3.74 (2H, t, J=5.0); C$^{13}$-NMR (CDCl$_3$, 75 MHz): δ=0.0, 2.2, 13.7, 23.2, 40.9, 65.6, 74.3.

EXAMPLE 10

Preparation of

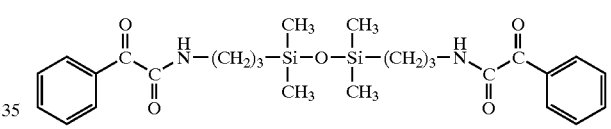

q=1, m=1, A=A'=IN-C(O)—NH—CH$_2$—Y—; IN is Phenyl-CO—, Y=—(CH$_2$)$_2$—, R$_1$=R$_1$'=R$_2$=R$_2$'=CH$_3$, R$_4$ is H.

2.2 equivalents (4.35 g) oxo-phenyl-acetic acid methyl ester and one equivalent (3 g) of amine (ABCR) of the following formula

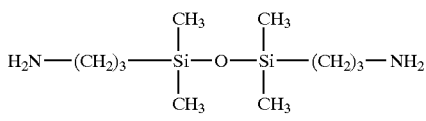

are dissolved in 30 mL diisopropylether at room temperature. 5 g of enzyme (Novozym® 435) are added. Total conversion is not achieved after 24 h (results of TLC), however, work up followed. The reaction mixture is filtered through a plug of celite to remove the biocatalyst and the solvent is evaporated. The residue is purified by flash chromatography (hexane/EtOAc, 4:1). Yield: 0.95 g, $R_f$ (hexane/EtOAc, 2:1)=0.65 $^1$H-NMR in ppm (CDCl$_3$, 300 MHz): δ=0.03 (12H, s), 0.048–0.53 (4H, m), 1.48–1.58 (4H, m), 3.25–3.31 (4H, m), 7.12 (2H, bs), 7.33–7.40(4H, m), 7.45–7.53 (2H, m), 8.18–8.23 (4H, m); C$^{13}$—NMR (CDCl$_3$, 75 MHz): δ=0.0, 13.2, 20.7, 41.9, 127.9, 130.6, 132.8, 133.8, 161.3, 187.4.

The invention claimed is:

1. A process for preparing organosilicon group containing photoinitiators of the formula I

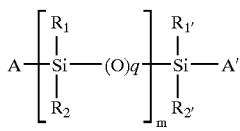

wherein
m is a number from 1 to 200;
q is 0 or 1;
A is IN-C(O)—O—CHR$_3$—Y— or IN-C(O)—NH—CHR$_3$—Y—;
A' is A or R$_1$';
R$_1$ and R$_1$', R$_2$ and R$_2$' independently of one another are C$_1$–C$_{18}$alkyl or phenyl or —(O)$_q$—SiR, R$_1$'R$_2$;
R$_3$ is hydrogen or C$_1$–C$_6$alkyl,
Y is a divalent group C$_1$–C$_{10}$alkylene, C$_2$–C$_{10}$alkenylene or —(CH$_2$)$_b$—O—(CH$_2$)$_a$—; a and b are each independently of the other a number of 1 to 6;
IN is a photolabile functional moiety of the formula II or III

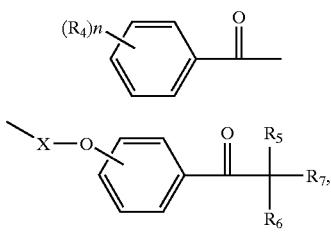

wherein
R$_4$ is hydrogen or —C(O)—C(O)—OH or —C(O)—C(O)—OC$_1$–C$_6$alkyl and n is 1–3;
R$_5$ and R$_6$ are C$_1$–C$_{12}$alkyl or together are cycloC$_5$–C$_7$alkyl;
R$_7$ is hydroxy, C$_1$–C$_6$alkoxy or morpholinyl;
X is —(CH$_2$)$_a$—, —(CH$_2$)$_b$—O—(CH$_2$)$_a$— or —(CH$_2$)$_b$—O—CO—(CH$_2$)$_a$—; a and b are each independently of the other a number of 1 to 6;
which process comprises
reacting a photolabile functional moiety containing a carboxy group (IN-COOH) or an alkoxycarbonyl group (IN-CO—OC$_1$–C$_6$alkyl) with a carbinol or amino terminated organosilicon compound of the formula IV

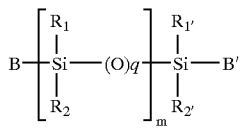

wherein m, R$_1$ and R$_1$', R$_2$ and R$_2$' are as defined above and
B is —Y—CHR$_3$—OH or —Y—CHR$_3$—NH$_2$;
B' is B or R$_1$',
in the presence of an enzyme which catalyzes the esterification, transesterification or amidation reaction.

2. A process according to claim 1, wherein
m is a number from 1 to 20;
q is 0 or 1;
A is a group

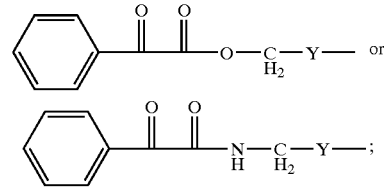

A' is A or R$_1$';
R$_1$ and R$_1$', R$_2$ and R$_2$' independently of one another are methyl, —O—Si(CH$_3$)$_3$ or —Si(CH$_3$)$_3$;
Y is a divalent group C$_1$–C$_{10}$alkylene, C$_2$–C$_{10}$alkenylene or —(CH$_2$)$_b$—O—(CH$_2$)$_a$—; a and b are each independently of the other a number of 1 to 6;
which process comprises
reacting a photolabile functional moiety containing a carboxy group (IN-COOH) or an alkoxycarbonyl group (IN-CO—OC$_1$–C$_6$alkyl) with a carbinol or amino terminated organosilicon compound of the formula IV

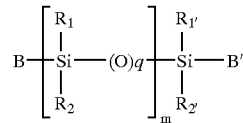

wherein m, R$_1$ and R$_1$', R$_2$ and R$_2$' are as defined above and
B is —Y—CH$_2$—OH or —Y—CH$_2$—NH$_2$;
B' is B or R$_1$',
in the presence of an enzyme selected from the group consisting of esterases, lipases and proteases.

3. A process according to claim 1, wherein
m is a number from 1 to 20;
q is 0 or 1;
A is a group of the formula IIIa or IIIb

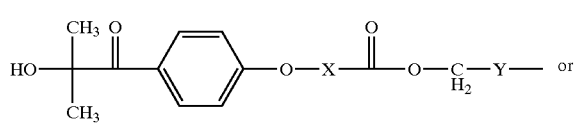

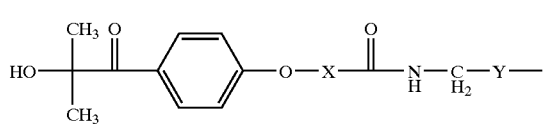

A' is A or R$_1$';
R$_1$ and R$_1$', R$_2$ and R$_2$' independently of one another are methyl, —O—Si(CH$_3$)$_3$ or —Si(CH$_3$)$_3$;
Y is a divalent group C$_1$–C$_{10}$alkylene, C$_2$–C$_{10}$alkenylene or —(CH$_2$)$_b$—O—(CH$_2$)$_a$—; a and b are each independently of the other a number of 1 to 6;

X is —(CH$_2$)$_a$—, —(CH$_2$)$_b$—O—(CH$_2$)$_a$— or —(CH$_2$)$_b$—O—CO—(CH$_2$)$_a$—; a and b are each independently of the other a number of 1 to 6;

which process comprises reacting a photolabile functional moiety containing a carboxy group (IN-COOH) or an alkoxycarbonyl group (IN-CO—OC$_1$–C$_6$alkyl) with a carbinol or amino terminated organosilicon compound of the formula IV

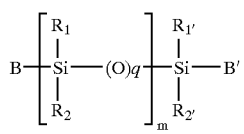

IV wherein m, R$_1$ and R$_1$', R$_2$ and R$_2$' are as defined above and

B is —Y—CH$_2$—OH or —Y—CH$_2$—NH$_2$;

B' is B or R$_1$', in the presence of an enzyme selected from the group consisting of esterases, lipases and proteases.

4. A process according to claim 1, wherein the enzyme is immobilized on a support.

5. A process according to claim 1, wherein the reaction is carried out at a temperature in the range from 25° C. to 75° C.

6. A process according to claim 2, wherein the enzyme is immobilized on a support.

7. A process according to claim 3, wherein the enzyme is immobilized on a support.

8. A process according to claim 2, wherein the reaction is carried out at a temperature in the range from 25° C. to 75° C.

9. A process according to claim 3, wherein the reaction is carried out at a temperature in the range from 25° C. to 75° C.

10. A process according to claim 4, wherein the reaction is carried out at a temperature in the range from 25° C. to 75° C.

11. A process according to claim 6, wherein the reaction is carried out at a temperature in the range from 25° C. to 75° C.

12. A process according to claim 7, wherein the reaction is carried out at a temperature in the range from 25° C. to 75° C.

* * * * *